US005604130A

United States Patent [19]

Warner et al.

[11] Patent Number: 5,604,130

[45] Date of Patent: Feb. 18, 1997

[54] RELEASABLE MULTIWELL PLATE COVER

[75] Inventors: Brian D. Warner, Martinez; Benjamin T. Nordell, Belmont; Bruce J. Richardson, Los Gatos; Amer El-Hage, Menlo Park, all of Calif.

[73] Assignees: Chiron Corporation, Emeryville; LJL Biosystems, Inc., Sunnyvale, both of Calif.

[21] Appl. No.: 451,025

[22] Filed: May 31, 1995

[51] Int. Cl.[6] .............................. C12M 1/02; C12M 1/38

[52] U.S. Cl. .............................. 435/286.7; 435/287.2; 435/288.4; 435/305.3; 422/99; 422/102; 220/523; 220/526

[58] Field of Search .............................. 435/283.1, 286.1, 435/286.2, 286.7, 287.2, 287.3, 288.3, 288.4, 288.7, 303.1, 303.3, 305.2, 305.3, 808; 422/63, 65, 99, 101, 102; 220/23.2, 23.4, 23.8, 23.83, 523, 526, 255, 359, 378; 100/54, 92, 211; 428/40, 163, 167, 172, 411.1, 446, 447, 450, 451, 465; 359/396, 398; 156/69; 277/207 R, 211, 213

[56] References Cited

U.S. PATENT DOCUMENTS

| | | | |
|---|---|---|---|
| 2,691,935 | 10/1954 | Zeiler et al. | 100/211 |
| 4,772,453 | 9/1988 | Lisenbee . | |
| 4,927,604 | 5/1990 | Mathus et al. . | |
| 5,056,427 | 10/1991 | Sakabe et al. | 100/211 |
| 5,192,503 | 3/1993 | McGrath et al. | 422/57 |
| 5,227,137 | 7/1993 | Monti et al. . | |
| 5,282,543 | 2/1994 | Picozza et al. | 220/255 |
| 5,342,581 | 8/1994 | Sanadi | 422/101 |
| 5,346,672 | 9/1994 | Stapleton et al. | 422/102 |
| 5,364,790 | 11/1994 | Atwood et al. | 435/288 |

*Primary Examiner*—William Beisner
*Attorney, Agent, or Firm*—Robert P. Blackburn; Kenneth M. Goldman; Peter J. Dehlinger

[57] ABSTRACT

A cover effective to releasably seal a multiwell container, such as a microtitration plate, is disclosed. The cover contains a pad, fashioned from a flexible polymer sheet, and a plurality of resiliently compressible ridges formed on the sheet. The ridges are deformable, such that application of pressure applied to the cover is effective to form a fluid-tight seal between the pad and the well openings. The ridges extend from the pad sufficiently to break the seal upon release of the pressure.

21 Claims, 6 Drawing Sheets

RELEASABLE MULTIWELL PLATE COVER

FIELD OF THE INVENTION

The present invention relates to a releasable cover used for sealing multiwell containers, such as microtitration plates, employed in automated multi-sample fluid handling systems.

BACKGROUND OF THE INVENTION

The efficiency with which various tests, reactions, assays and the like in biology, clinical diagnostics, and other areas, has been greatly increased by adoption of parallel sample handling techniques. Specific examples include polymerase chain reaction (PCR) techniques, enzyme-linked immunesorbent assay (ELISA), enzyme immune assay (EIA), radioimmune assay (RIA), membrane capture assays, cell washing, enzyme assays, including receptor binding assays, and the like. In most of these cases, the samples can be processed in multiwell plates. One of the most common formats is a 96-well plate, where the wells are arranged in a matrix having 8 rows and 12 columns.

In an effort to increase efficiency even further, and to reduce manual repetitive tasks performed by laboratory technicians, a number of multi-sample handling tasks are being adapted for use with automated systems. Such systems typically employ multiwell plates for storing, reacting and/or analyzing liquid samples, and generally include a liquid-handling apparatus, which transfers fluid between selected containers and/or wells, and an automated plate handling apparatus to manipulate the multiwell plates containing the samples. Examples of automated systems include robots for automated assembly and thermal cycling of PCR reaction, luminometers, plate readers and the like.

Samples handled in an automated system may need to be heated and/or agitated at specific points during the processing cycle. Such operations typically require the wells containing the samples to be sealed. The seals usually need to be fluid-tight to prevent loss of sample fluid, particularly in cases where the contents of the wells are heated (creating a positive pressure in the well). Following such a heating and/or agitation step, the plates may need to be uncovered (e.g., to add other reaction components to the wells or to remove reacted samples). In many cases, such as when a heated plate has been cooled prior to opening, the cover may be positively adhered to the surface of the multiwell plate. During cover removal, this adhesion, which may be due to polymer adhesive effects or pressure effects due to escape of some gases during heating and negative pressure on cooling, may result in (i) a dislodging of the plate from the tray holder, (ii) a sudden plate movement which spills sample contents, and/or (iii) a splashing of well contents onto the cover and/or other wells.

Accordingly, it would be desirable to have a cover capable of effectively sealing the wells of a multiwell plate in an automated system. The seal should be effective to prevent loss of well contents during heating or agitation, yet be able to be released at will without disrupting samples contained in the wells, and without the use of unnecessary force or unduly complicated systems.

SUMMARY OF THE INVENTION

In one aspect, the present invention includes a pad for use in sealing wells having openings in the upper surface of a multi-well plate, such as a microtitration plate. The pad is composed of an elastic, compressible and resilient sheet, such as a flexible polymer sheet, defining a planar expanse adapted to cover the wells in the plate. Formed on the expanse is a plurality of resiliently compressible ridges adapted to seat over the openings of wells when the pad is placed operatively over the plate. With the application of a substantially uniform pressure to the side of the sheet opposite the expanse, the ridges are deformed to form a substantially fluid-tight seal between the expanse and the well openings. The ridges extend from the expanse sufficiently to break the seal upon release of the pressure.

In one embodiment, the sheet and ridges forming the pad are formed integrally of a compressible rubber material or polymeric elastomer, such as silicon rubber or polyurethane rubber, the sheet has a thickness of between about 90 and 150 mils, and the ridges, in a relaxed (non-compressed) state, extend between about 0.005 and 0.030 inches from the surface of the planar expanse. In another embodiment, a hydrophobic film (e.g., high density polyethylene; HDPE) covers the expanse and ridges. The film, which has a preferred thickness between about 1–5 mils, may be coated directly on the pad and ridges, or it may be disposed between the expanse and the well openings as a separate sheet.

The pad may be designed for use with a plate whose well openings are defined by raised rims extending from the surface of the plate. Here the ridges may be arranged to form a substantially rectangular array on the expanse, where points of ridge intersections in the array correspond to positions of well openings in the plate. Alternatively, the pad may be designed for use with a plate whose well openings are substantially coplanar with the surface of the plate. In this embodiment, the ridges may be discontinuous across surface regions of the expanse corresponding to surface regions of the plate between well openings.

In another aspect, the invention includes an automated plate handling apparatus of the type having a tray for receiving a multiwell plate, such as a microtitration plate, having a plurality of wells with upper planar openings, sample-handling structure for heating and/or shaking the plate, and a sealing assembly including a cover and structure for moving the cover from a retracted position toward a sealing position. The pad is attached to the cover and is used in sealing the wells of the plate, when the cover is moved to its sealing position, at which the pad is pressed against the surface of the plate. The pad in the apparatus has the construction and features of the pad described above.

These and other objects and features of the invention will be more fully appreciated when the following detailed description of the invention is read in conjunction with the accompanying drawings.

DETAILED DESCRIPTION OF THE INVENTION

Figure 1:
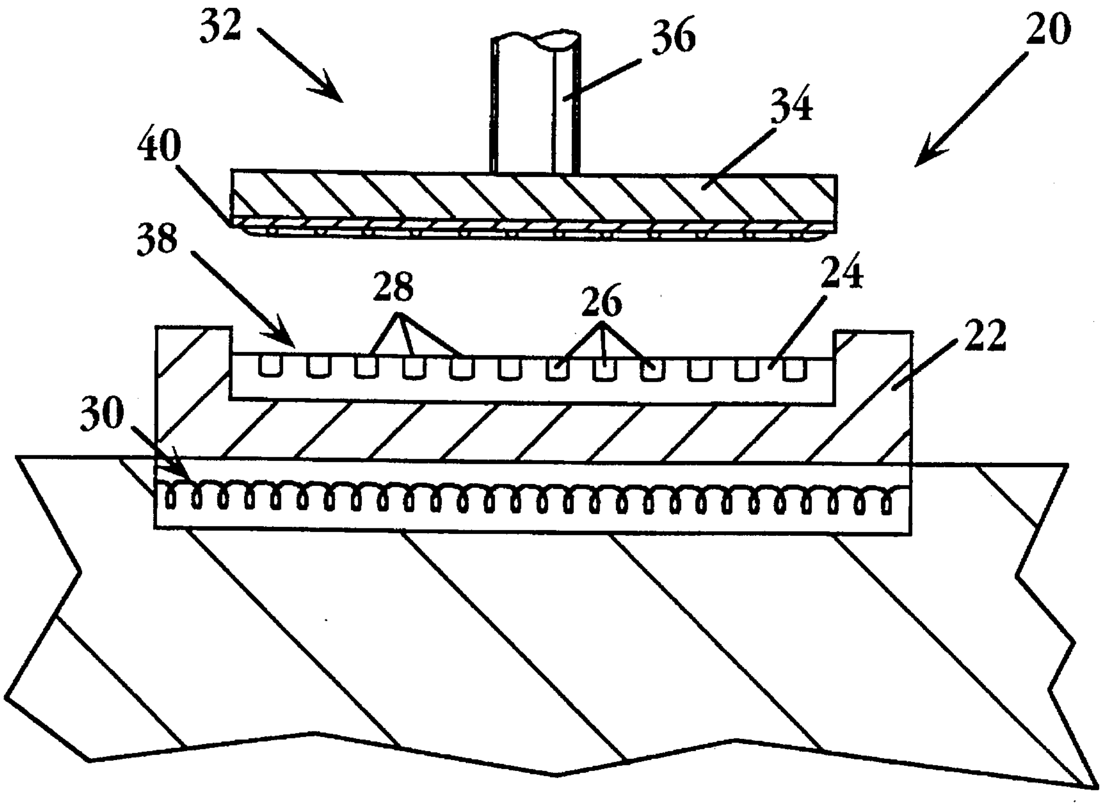
FIG. 1 is a simplified head-on view of a sample handling apparatus which employs a sealing pad constructed in accordance with the invention.

FIG. 1 illustrates, in a head-on view, an automated plate handling apparatus 20. The apparatus has a tray 22 for receiving a multiwell plate 24, such as a microtitration plate, which has a plurality of wells 26 with upper planar openings 28. The apparatus also includes a heater 30 for heating the plate, and a sealing assembly 32. The sealing assembly includes a cover 34 and a piston 36 for moving the cover from a retracted position toward a sealing position. A pad 40 is attached to the cover and is used in sealing the wells of the plate when the cover is moved to its sealing position. When the cover is in the sealing position, the pad is pressed against the surface 38 of the plate, effectively sealing the openings of the wells. The construction and unique features of the pad in the apparatus are described below. These features enable the pad to seal a multiwell plate when substantially uniform pressure is applied to the side of the pad opposite the wells, and to unseal the plate when the pressure is removed.

The automated plate handling apparatus described above may be a luminometer, PCR robot, EIA processing instrument, generic plate incubator or the like. The multiwell plate is positioned in the tray of the apparatus such that it is correctly aligned with the cover. The plate may also be partially or completely immobilized in the apparatus, such that vibrations or movement of the apparatus do not disturb the alignment of the cover/pad and the plate.

Pads of the present invention are particularly advantageous when used in an automated plate handling apparatus having a sample handling means for heating or shaking the plate, where the heating and/or shaking requires the plate to be sealed. The heater 30 described above is an exemplary sample handling means for heating the plate. Other sample handling means contemplated or use with the present invention are those effective to shake the plate, such as shakers, mixers, agitators and the like. It will be appreciated that both heating and shaking sample handling means may be employed in a single automated plate handling apparatus used according to the present invention.

The piston 36 described above is an exemplary means for moving the cover between a retracted position and a sealing position. To seal the wells of a plate, the piston moves the cover down into the cover's sealing position. Other means may be employed for moving the cover between sealing and retracted positions. For example, the cover may be snapped to the plate, providing a self-contained easily transportable unit. In this case, the sealing position is when snaps of the cover are engaged, and the cover is firmly attached to the plate. The retracted position is when the snaps are disengaged, allowing the cover to be lifted off the plate. Alternatively, the cover may be operatively attached to the apparatus through, for example, a retractable arm. When engaged in the sealing position, the arm is in an extended position, pressing the cover and attached pad against the top surface of the multiwell plate.

Figure 2A:
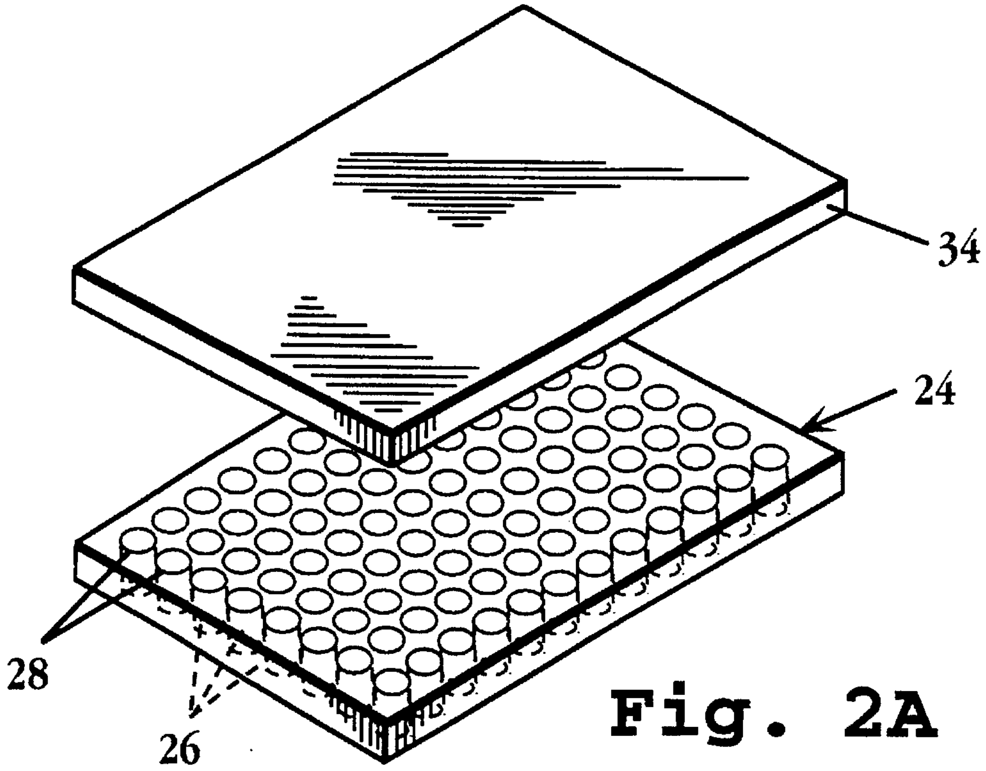
FIG. 2A is a top perspective view of a cover containing a pad of the present invention positioned over a multiwell plate.
Figure 2B:
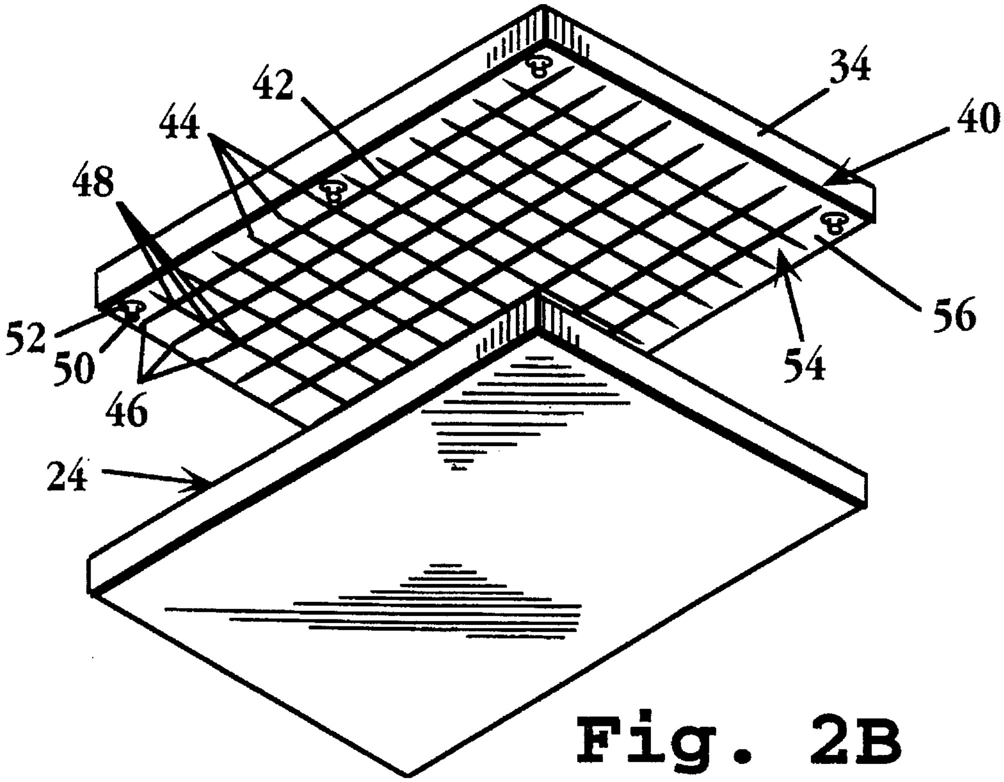
FIG. 2B is a bottom perspective view of a cover and plate shown in FIG. 2A.

FIGS. 2A and 2B illustrate, in perspective views, the relationship of a cover 34 containing a pad 40 of the present invention and a corresponding multiwell plate 24. The pad comprises a flexible polymer sheet 54, which defines a planar expanse 56 adapted to cover the wells 26 in the plate 24. Formed on the expanse is an array 42 of resiliently compressible ridges, including ridges 44 extending in a width-wise direction, and ridges 46 extending in a length-wise direction. The ridges are adapted to seal over the openings 28 of the wells (i.e., the intersections 48 of orthogonal ridges correspond to openings 28 of wells in the underlying plate 24) with the pad placed operatively over the plate. While the ridges in this embodiment of the invention are arranged in a rectangular array, it will be appreciated that other ridge arrangements, such as those described in relation to FIGS. 7–10, below, may be employed.

The pad is attached to the cover by an attachment means. In the embodiment shown in FIG. 2B, the attachment means comprise nubs, or protrusions 50 from the pad side of the cover which engage corresponding holes 52 in the sheet 54. The sheet is retained on the nubs by outward-facing notches in the nubs. Other attachment means may be employed, including an adhesive applied between the cover-facing (back) side of the pad and the pad-facing side of the cover, vacuum applied to the back side of the pad through ports in the cover, and the like.

The length and width of the pad are dimensioned to cover the surface of a selected multiwell plate. A common multiwell format is the 96-well plate, in which the wells are arranged in an eight by twelve array measuring approximately 3" by 4.5". The invention may, of course, be used with other multiwell formats, as described below. It will be understood that pads may be designed to cover only a portion of a multiwell plate, and that a plurality of such pads may be employed together to cover the entire plate. This arrangement enables, for example, the addition of a reagent to a subset of wells, while the remaining wells remain covered.

The cover 34 illustrated in FIGS. 2A and 2B is a rigid, uniform planar element having a length and width corresponding to those of the pad. Other types of covers are equally suitable for use with pads of the present invention. For example, the cover may comprise a frame, open in the center, with attachment means such as the protrusions 28, along the edges. The pad may be suspended in such a frame "cover" and sealed onto a multiwell plate by the action of a separate "pressure" element, such as a press dimensioned to fit inside the frame and apply substantially uniform pressure to the pad. Covers used with the present invention may also be attached directly to the plate when in the sealing position, rather than to the apparatus. Such covers may be advantageous, for example, in applications which require the wells to be sealed during agitation of the sample. A low-mass cover snapped directly to the plate may interfere only minimally with the agitation of the plate.

Figure 3:
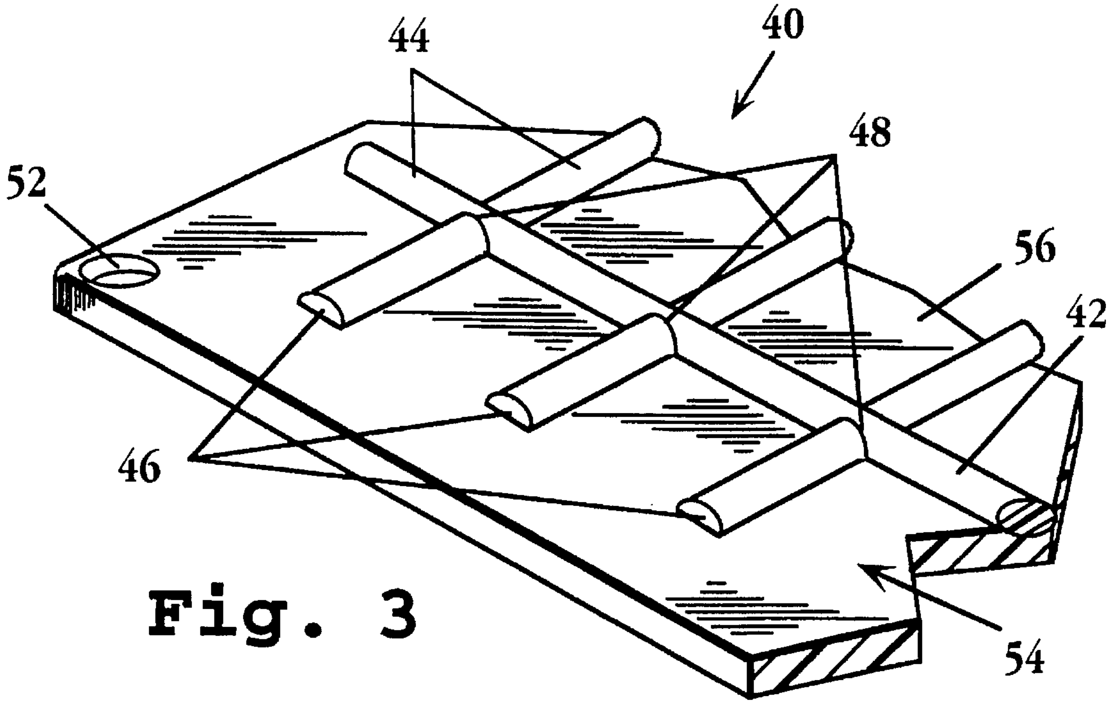
FIG. 3 is an enlarged, fragmentary perspective view of a portion of the pad shown in FIG. 2B.

FIG. 3 illustrates, in a perspective view, a pad 40 constructed in accordance with the present invention. The pad is constructed of a flexible polymer sheet 54 defining a planar expanse 56, and in the embodiment shown, includes a rectangular array 42 of ridges, such as parallel ridges 46 extending in a lengthwise direction, and ridges 44 extending in a width-wise direction. The array of ridges is preferably formed integrally with the sheet, i.e., as a single molded polymeric article. The polymer sheet 54 and ridges 44, 46 may be composed of a variety of flexible polymers (polymeric elastomers), such as natural rubber, silicone rubber, polyurethane rubber, and the like. The sheet may have a thickness ranging from about 0.90 mm to about 1.50 mm.

As is discussed below, the function of the ridges, which are preferably deformable and resilient, is to facilitate the breaking of a seal between the pad and the wells of a multiwell plate in the absence of substantially uniform downward pressure on the pad. Ridges effective to break the seal may have any of variety of profiles, including semi-circular or semi-oval (as illustrated in FIG. 3), square, triangular, and the like.

Figure 4:
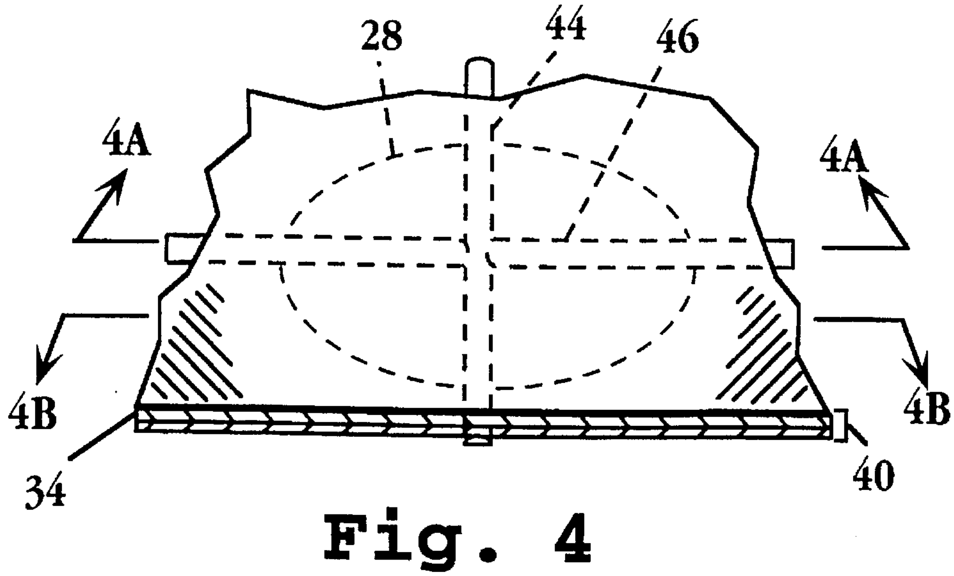
FIG. 4 is an enlarged, fragmentary perspective view of a portion of a pad of the present invention in relation to a cover to which it is attached and the opening of a well over which the pad is positioned.

FIG. 4 illustrates, in a perspective view, a pad 40 with ridges 44, 46 attached to a cover 34 and engaged with the opening 28 of a well in a multiwell plate. The opening of the well 28, and portions of the ridges 44, 46 are indicated as dotted lines.

Figure 5A:
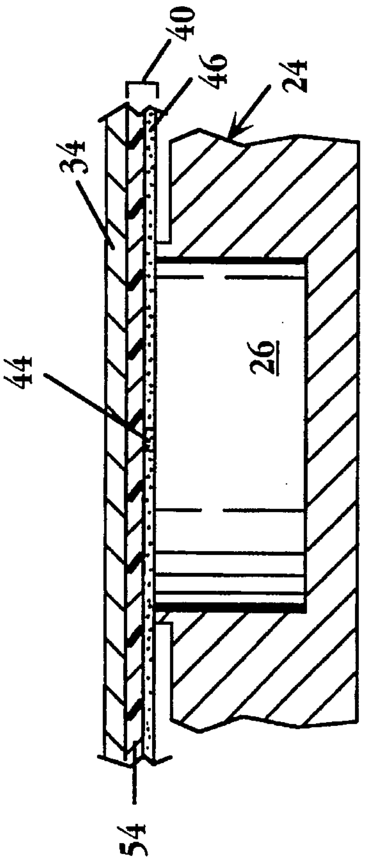
FIG. 5A is a cross-sectional view taken along line 4A—4A in FIG. 4, and a showing a portion of the plate which is covered by the pad shown in FIG. 4.
Figure 5B:
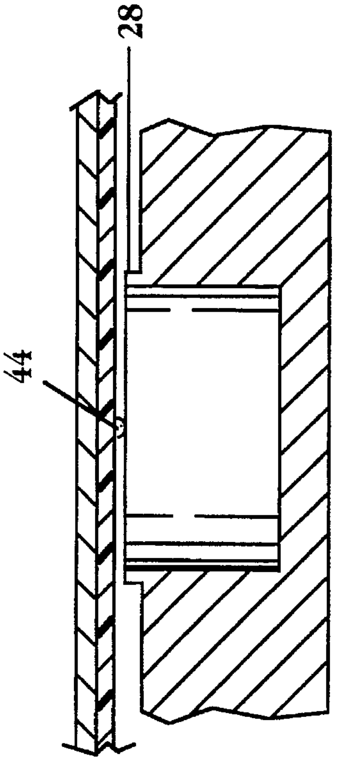
FIG. 5B is a cross-sectional view like that of FIG. 5A, but taken along line 4B—4B in FIG. 4.
Figure 5C:
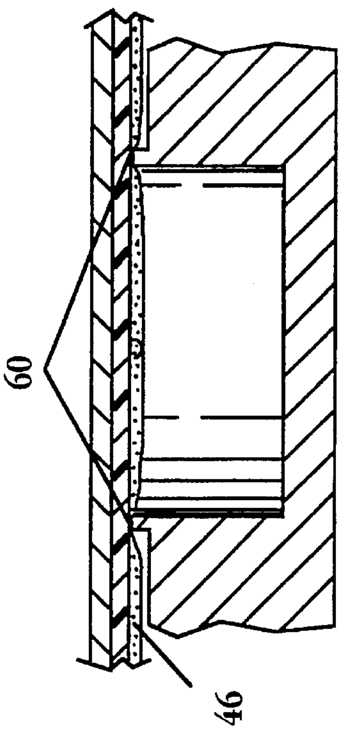
FIGS. 5C and 5D are sectional views identical to those of FIGS. 5A and 5B, respectively, but showing deformation of pad ridges and a formed seal when a sealing pressure is applied to the pad.
Figure 5D:
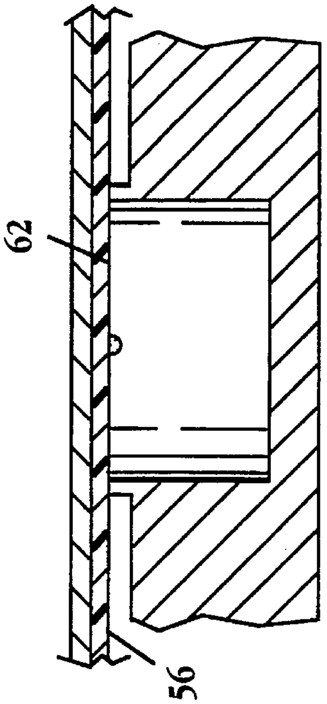

FIGS. 5A, 5B, 5C and 5D illustrate side views of the cover and plate shown in FIG. 4. The relationship of the components shown in FIGS. 5A and 5B is as it exists in the absence of pressure applied to the upper side of the cover, while the relationship of the components shown in FIGS. 5C and 5D is as it exists in the presence of pressure applied to the upper side of the cover.

FIG. 5A illustrates the engaged pad in a sectional view as seen from a plane along line 4A—4A in FIG. 4, and showing a portion of the plate which is covered by the pad shown in FIG. 4. The plane bisects a ridge 46 lengthwise, which is thus seen from its center as a linear segment just beneath the sheet 54. Since no downward pressure is applied, this ridge rests on top of the rim or edge of the well. The plane also bisects the orthogonal ridge 44 cross-wise, which is seen as an oval at the top center of the well.

FIG. 5B illustrates the engaged pad in a sectional view as seen from a plane along line 4B—4B in FIG. 4. off center of the well. Only the orthogonal ridge, 44, is seen in this view. It can be appreciated that, in absence of downward pressure, the ridges support the bulk of the sheet 54 above the opening 28 of the well, such that the inside of the well is in open communication with the external environment.

The elements illustrated in FIGS. 5A and 5B are shown in FIGS. 5C and 5D, respectively, in the presence of pressure, or a downward force, applied to the cover. Because the ridges are deformable, the downward force results in a compression of the ridges in the regions where the ridges contact the edge of the opening of a well. The compression is seen in FIG. 5C at the contacts 60 between the ridge 46 and the rim of the well. One effect of this compression, seen in FIG. 5D, is the formation of a substantially fluid-tight seal 62 between the expanse 56 and the well opening.

The ridges preferably extend from the expanse far enough to break a seal, upon release of downward pressure, even under conditions where the contents of the wells have been heated and then cooled (circumstances which often result in decreased pressure inside the well), but not so far that the formation of a seal is precluded in the presence of adequate downward pressure. The amount of pressure applied to the cover depends on a number of factors, including the size and number of ridges on the pad, the deformability of the pad material, whether or not an extra sheet, as described below, is disposed between the ridges and the wells, the number of wells and the like. For example, other factors being equal, the greater the fraction of the sealing surface (defined as the contact region between a smooth engaged pad, with the cover in the sealing position, and the rim or edge of a well opening) occupied by ridges, the more pressure is needed to obtain a seal, but the more effective the ridges are at breaking the seal in the absence of pressure.

The degree of seal-breaking potential (i.e., the number, dimensions and physical characteristics of the ridges) is typically dictated by the specific application. For example, in applications where the plate contains an aqueous solution and is covered merely for purposes of agitation, only a modest degree of seal-breaking potential may be required. Accordingly, the ridge characteristics in such an application (e.g., ridge height of 0.005") may allow the establishment of a seal with relatively low pressures. Alternatively, in applications where the plate is heated for a prolonged period, and needs to be opened after cooling to, e.g., at 4° C., the characteristics of ridges effective to break the seal may be such that a substantial downward force is required to establish the seal in the first place.

In the case of a pad with a thickness of 0.059", fashioned of silicone rubber, adapted to seal the wells in a 96-well plate, and containing ridges having roughly a semi-circular cross-section and protruding approximately 0.0059" from the pad surface, a pressure of approximately 15 psi, applied to a substantially rigid cover adapted to receive the pad, is sufficient to seal the wells. The ridges in such a pad are effective to break a seal following a 24 hour incubation at 63° C. with 200 μl of fluid per well. The pad is effective to retain over 90% of the initial well volume during such an incubation.

Pads of the present invention may be produced from a variety of flexible polymer materials, such as polymeric elastomers. As stated above, the material is preferably flexible, compliant and resilient. Exemplary materials include silicone rubber and polyurethane rubber. Due to its physical and thermal characteristics, silicone rubber is particularly suitable for applications where the pads encounter temperature extremes. Further, clear silicone rubber pads may be fashioned from Food and Drug Administration (FDA) grades of starting material. Such pads are reusable and easy to inspect for defects resulting from manufacture or use. An exemplary silicone rubber is 45 durometer class 6 silicone rubber (General Electric Corp., Fairfield, Conn.).

Figure 6A:
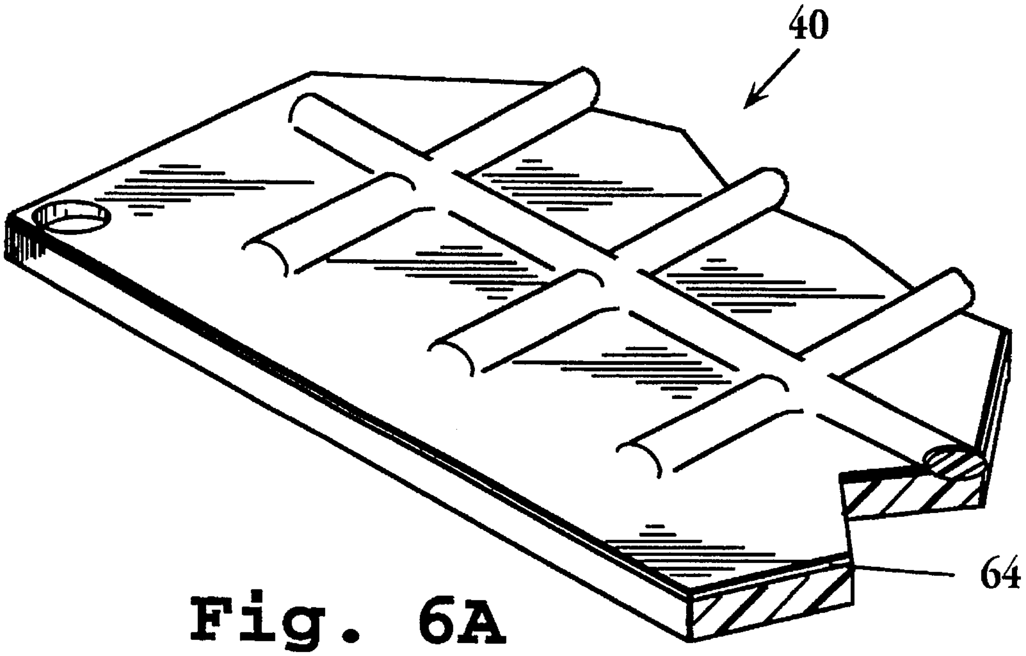
FIG. 6A is an enlarged, fragmentary perspective view of a portion of a pad coated with a hydrophobic film.
Figure 6B:
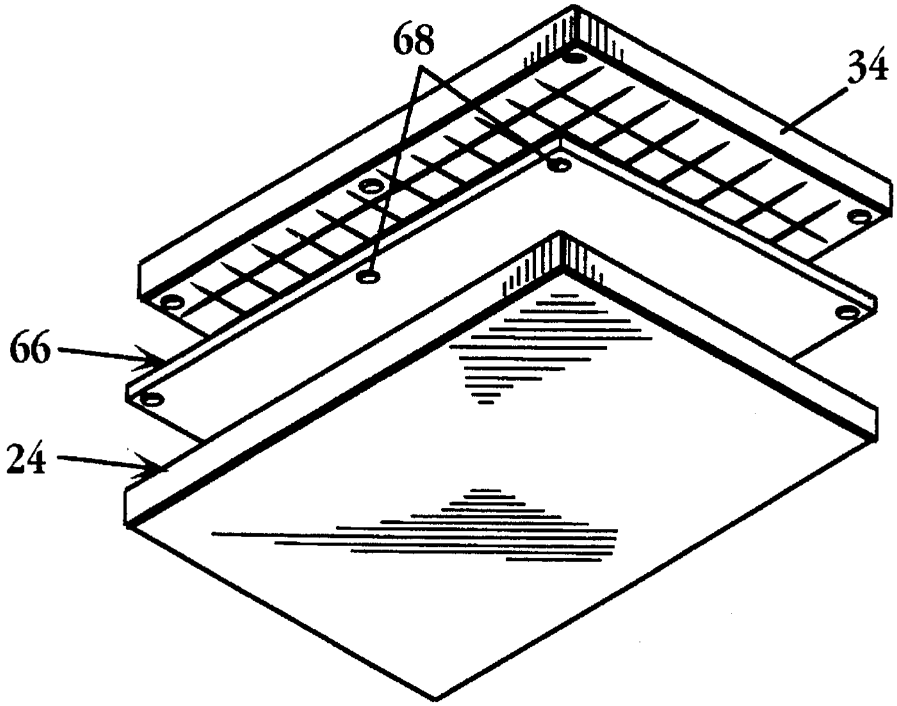
FIG. 6B shows a cover and plate shown in FIG. 2B, with a hydrophobic film disposed between the cover and the plate.

Also included in the present invention is a pad which includes a film of hydrophobic material, such as high density polyethylene (HDPE) disposed between the expanse and the wells in a multiwell plate. FIGS. 6A and 6B illustrate 2 exemplary embodiments. In FIG. 6A, the film 64 is formed directly on the expanse and ridges of the pad (e.g., by spray-coating), while in FIG. 6B, it is a separate sheet 66 disposed between the expanse 56 and the well openings of the plate 24. In the case where the film is a separate element, it may further contain an attachment means, such as the holes 68 shown.

The film serves several functions. First, it is less permeable to water vapor than an unmodified silicone rubber pad, and thus enables a greater retention of the well contents. Further, the hydrophobic coating may facilitate washing of the cover assembly so that a single cover may be used with several plates containing different samples. Alternatively, the sheet of film may be disposable, so that a new sheet of film is inserted each time a new plate is processed. The latter approach may reduce operating costs in cases where a fresh sealing surface is required for each new plate, since only the film, instead of the entire pad, needs to be replaced between plates.

As indicated above, pads of the present invention may be produced for use with a variety of multiwell plate formats, including but not limited to 6-well plates, 12-well plates, 24-well plates, 36-well plates, 48-well plates, 96-well plates, 384-well plates, and the like. Further, the arrangement of ridges in relation to the wells may adopt a range of formats. Several examples are illustrated in FIGS. 7, 8, 9 and 10. In each of these fragmentary plan views, a portion of a pad is shown, along with the arrangement of the ridges relative to underlying wells in a microtitration plate. The openings of the wells 28 are indicated by dashed lines in the shape of a circles.

Figure 7:
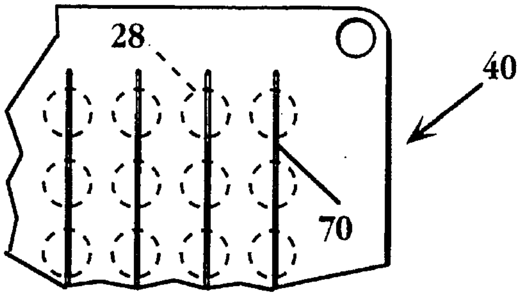
FIGS. 7–10 are plan views of four sealing pads constructed according to alternative embodiments of invention.
Figure 8:
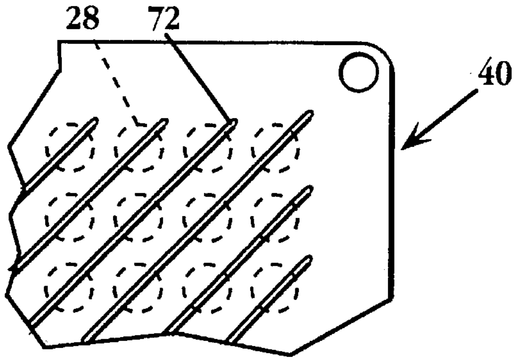

FIG. 7 shows an embodiment of the invention where each well is bisected by only a single ridge. The ridges 70 may correspond to the columns of wells in a multiwell plate, as shown, or to rows. In other embodiments, the ridges may be arranged to intersect wells in a diagonal fashion (72; FIG. 8).

Figure 9:
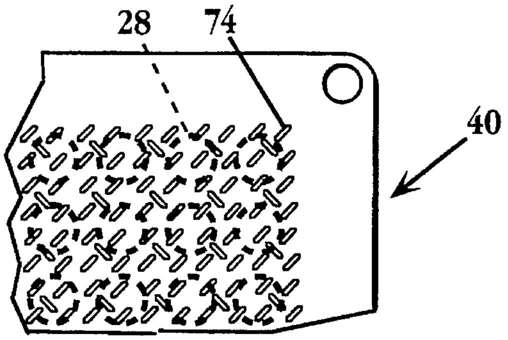
Figure 10:
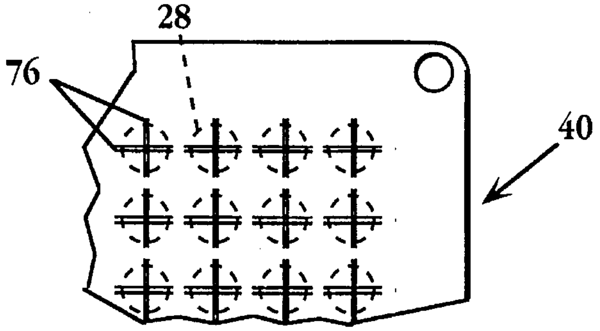

Alternatively, the ridges may be discontinuous. One such embodiment is shown in FIG. 9. Here, the ridges 74 are short ovals arranged at a high enough spacial frequency to insure that, when the pad is in an engaged position, the edge of each well is contacted by at least one ridge. A discontinuous pattern may also be beneficial in cases where the well openings are coplanar with the surface of the plate, as illustrated in FIG. 10. In such arrangements, the ridges 76 may be positioned so that one or a few ridges just span the contact region between the pad and the edge of a well. By limiting the extent of the ridges in regions of the plate between well openings, the pressure required to form a seal is maintained at a reasonable level. If a higher "release force" is desired, the portion of the ridge extending into regions of the plate between well openings may be increased.

Although the invention has been described with respect to certain embodiments, configurations and applications, it will be apparent to those skilled in the art that various modifications and changes may be made without departing from the invention.

It is claimed:

1. A pad for use in sealing wells having openings in the upper surface of a multi-well plate, comprising a flexible polymer sheet defining a planar expanse adapted to cover the wells in the plate, and formed on said expanse, a plurality of resiliently compressible ridges adapted to seat over the openings of said wells, with the pad placed operatively over the plate, said ridges being deformable, with application of a substantially uniform pressure applied to the side of the sheet opposite said expanse, to form a substantially fluid-tight seal between said expanse and such well openings, and said ridges extending from said expanse sufficiently to break said seal upon release of said pressure.

2. The pad of claim 1, wherein said sheet and ridges are formed integrally of a compressible rubber material, said sheet has a thickness between about 90 and 150 mils, and said ridges in a relaxed state extend between about 0.005 and 0.030 inches from the surface of said planar expanse.

3. The pad of claim 2, wherein said rubber material is silicon rubber or polyurethane rubber.

4. The pad of claim 2, which further includes a hydrophobic film covering said expanse and ridges, and having a thickness between about 1–4 mils.

5. The pad of claim 4, wherein said film contains high density polyethylene (HDPE).

6. The pad of claim 2, wherein said pad further includes a hydrophobic film disposed between said expanse and said well openings, and having a thickness between about 2–5 mils.

7. The pad of claim 6, wherein said film contains high density polyethylene (HDPE).

8. The pad of claim 1, for use with a plate whose well openings are substantially coplanar with the surface of the plate, wherein said ridges are discontinuous across surface regions of said expanse corresponding to surface regions of the plate between well openings.

9. The pad of claim 1, for use with a plate whose well openings are defined by raised rims extending from the surface of the plate.

10. The pad of claim 9, wherein the ridges form a rectangular array on the expanse, and points of ridge intersections in the array correspond to positions of well openings in the plate.

11. In an automated plate handling apparatus of the type having a tray for receiving a multiwell plate having a plurality of wells with upper planar openings, sample-handling means for heating or shaking the wells, and a sealing assembly including a cover and means for moving said cover from a retracted position toward a sealing position, a pad attached to said cover for use in sealing the wells of said plate, with the cover moved toward its sealing position, at which the pad is pressed against the surface of the plate, where in the improvement comprises, said pad comprising a flexible polymer sheet defining a planar expanse dimensioned to cover the wells in the plate, and formed on said expanse, a plurality of resiliently compressible ridges adapted to seat over the openings of said wells, said ridges being deformable, as the cover is moved toward its sealing position, to form a substantially fluid-tight seal between said expanse and such well openings, said ridges extending from said expanse sufficiently to break said seal upon movement of the cover toward its retracted position.

12. The apparatus of claim 11, wherein said sheet and ridges are formed integrally of a compressible rubber material, said sheet has a thickness between about 90 and 150 mils, and said ridges in a relaxed state extend between about 5 and 30 mils from the surface of said planar expanse.

13. The apparatus of claim 12, wherein said rubber material is silicon rubber or polyurethane rubber.

14. The apparatus of claim 12, which further includes a hydrophobic film covering said expanse and ridges, and having a thickness between about 1–4 mils.

15. The apparatus of claim 14, wherein said film contains high density polyethylene (HDPE).

16. The apparatus of claim 12, wherein said pad further includes a hydrophobic film disposed between said expanse and said well openings, and having a thickness between about 2–5 mils.

17. The apparatus of claim 16, wherein said film contains high density polyethylene (HDPE).

18. The apparatus of claim 11, for use with a plate whose well openings are defined by raised rims extending from the surface of the plate.

19. The apparatus of claim 18, wherein the ridges form a rectangular array on the expanse, and points of ridge intersections in the array correspond to positions of well openings in the plate.

20. The apparatus of claim 11, for use with a plate whose well openings are substantially coplanar with the surface of the plate, wherein said ridges are discontinuous across surface regions of said expanse corresponding to surface regions of the plate between well openings.

21. The apparatus of claim 11, wherein the plate handling apparatus is a luminometer.

* * * * *